United States Patent
Hendrix et al.

(10) Patent No.: US 12,089,993 B1
(45) Date of Patent: Sep. 17, 2024

(54) SELF-CENTERING RADIAL ENCODING SCANNER AND RELATED SYSTEMS AND METHODS

(71) Applicant: Top Notch EDM Services LLC, Conroe, TX (US)

(72) Inventors: Matthew O. Hendrix, Willis, TX (US); Jason E. Landers, Willis, TX (US); Christopher A. Well, Conroe, TX (US); Justin A. Kelly, Conroe, TX (US)

(73) Assignee: Top Notch EDM Services LLC, Conroe, TX (US)

( * ) Notice: Subject to any disclaimer, the term of this patent is extended or adjusted under 35 U.S.C. 154(b) by 0 days.

(21) Appl. No.: 18/374,797

(22) Filed: Sep. 29, 2023

Related U.S. Application Data

(60) Provisional application No. 63/528,068, filed on Jul. 20, 2023.

(51) Int. Cl.
*A61B 8/13* (2006.01)
*A61B 8/00* (2006.01)

(52) U.S. Cl.
CPC .................. *A61B 8/4461* (2013.01)

(58) Field of Classification Search
CPC ....... A61B 8/4461; A61B 8/54; A61B 8/4488; G10K 11/352; G10K 11/004; G01N 29/24; G01N 29/265; G01N 29/0654; G01N 29/225; G01N 29/221; G01N 29/26
See application file for complete search history.

(56) References Cited

U.S. PATENT DOCUMENTS

| | | | |
|---|---|---|---|
| 3,171,309 A | 3/1965 | Cloutier | |
| 4,257,289 A | 3/1981 | Groothius | |
| 5,076,025 A * | 12/1991 | Reeble | B24B 9/007 |
| | | | 269/48.1 |
| 10,537,940 B2 | 1/2020 | Atin et al. | |
| 2022/0401067 A1 * | 12/2022 | Yoshida | A61B 8/4245 |

FOREIGN PATENT DOCUMENTS

| | | |
|---|---|---|
| CN | 113447571 A | 9/2021 |
| DE | 7034725 U | 9/1970 |
| DE | 2164337 A1 | 6/1973 |

* cited by examiner

*Primary Examiner* — Tarun Sinha
(74) *Attorney, Agent, or Firm* — Quisenberry Law PLLC

(57) ABSTRACT

Non-destructive testing scanner devices are disclosed to enable examination of portions of a part to be examined that presently-available scanners are not designed for. A scanner may include a central shaft having an assembly of engagement members adapted to engage an inner bore of a part and thereby support the central shaft along a central axis of the bore. An encoder may be supported by the central shaft. An ultrasonic probe may also be supported by the central shaft. The probe may be positioned on a surface of the part to be examined and moved in a circular path around the central shaft, and in so doing may cause a drive shaft on the encoder to rotate. The probe and encoder may be electrically connected to an instrument to convey data from the probe and from the encoder representative of characteristics of the surface being examined to the instrument.

16 Claims, 4 Drawing Sheets

SELF-CENTERING RADIAL ENCODING SCANNER AND RELATED SYSTEMS AND METHODS

RELATED APPLICATIONS

This application claims the benefit of U.S. Provisional Application No. 63/528,068, filed Jul. 20, 2023, the contents of which are fully incorporated herein by reference.

BACKGROUND OF THE INVENTIONS

1. Field of the Inventions

The present inventions generally pertain to industrial testing equipment and processes, and more particularly to devices for use in nondestructive testing (NDT) that uses ultrasonic technology to examine the quality and characteristics of a metal part or component, such as a pipe.

2. Description of the Related Art

In the Nondestructive Testing (NDT) industry, ultrasonic testing is a widely used method for gathering data that attests to the quality of a part or components. Such data that can be gathered through use of an ultrasonic transducer may include thickness measurements, flaw mapping, and flaw sizing of raw materials and/or welds. For repeatability it becomes necessary to encode the position of the ultrasonic transducer for ultrasonic inspections relative to the part or component being examined. There are many different options for scanning equipment that can encode around the inner diameter (ID) or outer diameter (OD) surface in the circumferential or axial position. However, such known scanning equipment cannot encode an end of a part or component, such as a pipe, or around a curved surface that is perpendicular to the pipe OD axis.

As will become apparent from the following descriptions and discussion, the present inventions encompass novel and unique solutions, including self centering radial encoding scanners, that can be used to encode bevel preps, buttered weld preps, nozzle welds, and the ends of parts and components, such as a flat or beveled end of a pipe.

SUMMARY OF THE INVENTIONS

In one aspect, the present inventions may include a scanner apparatus comprising: a central shaft; three engagement members supported by the central shaft, each engagement member being moveable between a first position and a second position; an encoder supported by the central shaft and having a drive shaft coupled to the central shaft; and an ultrasonic probe supported by and spaced apart from the central shaft, whereby movement of the ultrasonic probe around the central shaft will cause the encoder to move around the central shaft and cause the encoder drive shaft to rotate. Another feature of this aspect of the present inventions may be that the ultrasonic probe moves in a first direction around the central shaft, and in response thereto the encoder drive shaft rotates in a second direction that is opposite to the first direction. Another feature of this aspect of the present inventions may be that the scanner apparatus may further include a slip collar having an internal passageway, wherein the central shaft extends through the internal passageway, the slip collar is disposed for slidable movement relative to the central shaft, and the three engagement members are supported by the slip collar. Another feature of this aspect of the present inventions may be that the scanner apparatus may further include three hinged leg members, each of the three hinged leg members being connected to the slip collar, each of the three engagement members being supported by one of the three hinged leg members. Another feature of this aspect of the present inventions may be that each of the three hinged leg members includes an upper arm and a lower arm, the upper arm having an upper end hingedly connected to the slip collar and a lower end hingedly connected to an upper end of the lower arm, the lower end of the upper arm and the upper end of the lower arm being hingedly connected to one of the three engagement members, and a lower end of the lower arm being hingedly supported the central shaft. Another feature of this aspect of the present inventions may be that the scanner apparatus may further include a spring disposed around the central shaft and positioned between the slip collar and a shoulder on the central shaft. Another feature of this aspect of the present inventions may be that the scanner apparatus may further include a threaded nut and a locking nut, the central shaft including a threaded portion, part of the threaded portion of the central shaft being positioned within the internal passageway of the slip collar, the threaded nut and the locking nut being threadably engaged with the threaded portion of the central shaft, the threaded nut being located for engagement with the slip collar, and the locking nut being located for engagement with the threaded nut. Another feature of this aspect of the present inventions may be that the scanner apparatus may further include a bracket having a central body member, the central body member having a longitudinal passageway therethrough, the central shaft extending through the longitudinal passageway, the bracket being rotatable relative to the central shaft, the encoder being connected to the bracket, and the ultrasonic probe being supported by the bracket. Another feature of this aspect of the present inventions may be that the scanner apparatus may further include an elongated arm having a first end hingedly attached to the bracket, and wherein the ultrasonic probe is connected to the elongated arm. Another feature of this aspect of the present inventions may be that the scanner apparatus may further include a fork having a first leg and a second leg, the ultrasonic probe being hingedly connected to the first leg and to the second leg, the fork being supported by the elongated bar and slidably moveable thereon. Another feature of this aspect of the present inventions may be that the scanner apparatus may further include an electronic instrument electrically connected to the encoder and to the ultrasonic probe.

In another aspect, the present invention may include a scanner apparatus comprising: a central shaft; three engagement members supported by the central shaft, each engagement member being moveable between a first position and a second position; a slip collar having an internal passageway, wherein the central shaft extends through the internal passageway, the slip collar is disposed for slidable movement relative to the central shaft, and the three engagement members are supported by the slip collar; a spring disposed around the central shaft and positioned between the slip collar and a shoulder on the central shaft; an encoder supported by the central shaft and having a drive shaft coupled to the central shaft; an elongated arm having a first end hingedly supported by the central shaft; and an ultrasonic probe connected to the elongated arm and spaced apart from the central shaft, whereby movement of the ultrasonic probe around the central shaft will cause the encoder to move around the central shaft and cause the encoder drive shaft to rotate. Another feature of this aspect of the present inventions may be that the ultrasonic probe moves in a first direction around the central shaft, and in response thereto the encoder drive shaft rotates in a second direction that is opposite to the first direction. Another feature of this aspect of the present inventions may be that the scanner apparatus may further include three hinged leg members, each of the three hinged leg members being connected to the slip collar, each of the three engagement members being supported by one of the three hinged leg members. Another feature of this aspect of the present inventions may be that each of the three hinged leg members includes an upper arm and a lower arm, the upper arm having an upper end hingedly connected to the slip collar and a lower end hingedly connected to an upper end of the lower arm, the lower end of the upper arm and the upper end of the lower arm being hingedly connected to one of the three engagement members, and a lower end of the lower arm being hingedly supported the central shaft. Another feature of this aspect of the present inventions may be that the scanner apparatus may further include a threaded nut and a locking nut, the central shaft including a threaded portion, part of the threaded portion of the central shaft being positioned within the internal passageway of the slip collar, the threaded nut and the locking nut being threadably engaged with the threaded portion of the central shaft, the threaded nut being located for engagement with the slip collar, and the locking nut being located for engagement with the threaded nut. Another feature of this aspect of the present inventions may be that the scanner apparatus may further include a bracket having a central body member, the central body member having a longitudinal passageway therethrough, the central shaft extending through the longitudinal passageway, the bracket being rotatable relative to the central shaft, the encoder being connected to the bracket, and the ultrasonic probe being supported by the bracket. Another feature of this aspect of the present inventions may be that the scanner apparatus may further include an electronic instrument electrically connected to the encoder and to the ultrasonic probe.

In another aspect, the present inventions may include a scanner apparatus comprising: a central shaft including a lower threaded section; a self-centering support slidably attached to a lower end of the central shaft, the self-centering support including a slip collar slidably attached to the central shaft, the slip collar including three hinged leg members, each hinged leg member having an engagement member; a spring disposed around the central shaft below the slip collar, and between the slip collar and a shoulder on the central shaft; an encoder fixedly mounted to a bracket rotatably mounted to an upper end of the central shaft, the encoder including a drive shaft connected to a drive pulley, the drive pulley being connected by a belt to a central pulley mounted to the central shaft; an elongated arm hingedly attached to the bracket; a fork attached to the arm, the fork having a first leg and a second leg; and an ultrasonic probe hingedly attached between the first leg and the second leg of the fork. Another feature of this aspect of the present inventions may be that the ultrasonic probe moves in a first direction around the central shaft, and in response thereto the encoder drive shaft rotates in a second direction that is opposite to the first direction.

Other features, aspects and advantages of the present inventions will become apparent from the following discussion and detailed description.

While the inventions will be described in connection with the preferred embodiments, it will be understood that the scope of protection is not intended to limit the inventions to those embodiments. On the contrary, the scope of protection is intended to cover all alternatives, modifications, and equivalents as may be included within the spirit and scope of the inventions as defined by the appended claims.

DETAILED DESCRIPTION OF THE INVENTION

The present inventions will be described in various representative embodiments, as explained below. However, the scope of the present inventions are not limited to any of the details of the embodiments discussed below. Reference should be made to the appended claims, each of which defines a separate and distinct invention that is part of the present inventions.

Figure 1:
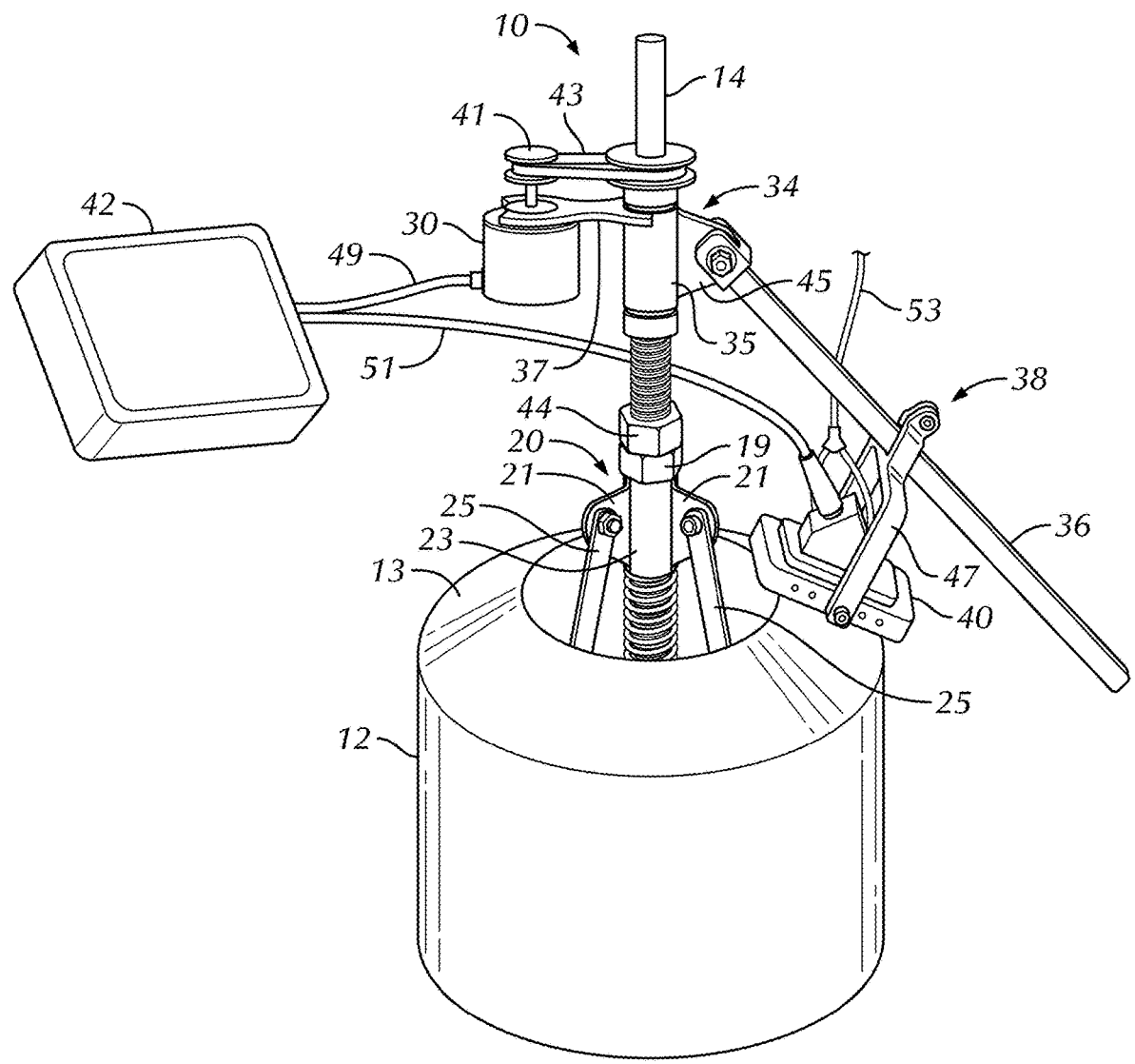
FIG. 1 is a perspective view of a specific embodiment of a scanner device constructed in accordance with one aspect of the present inventions, and mounted to a part having a beveled end to be examined.
Figure 2:
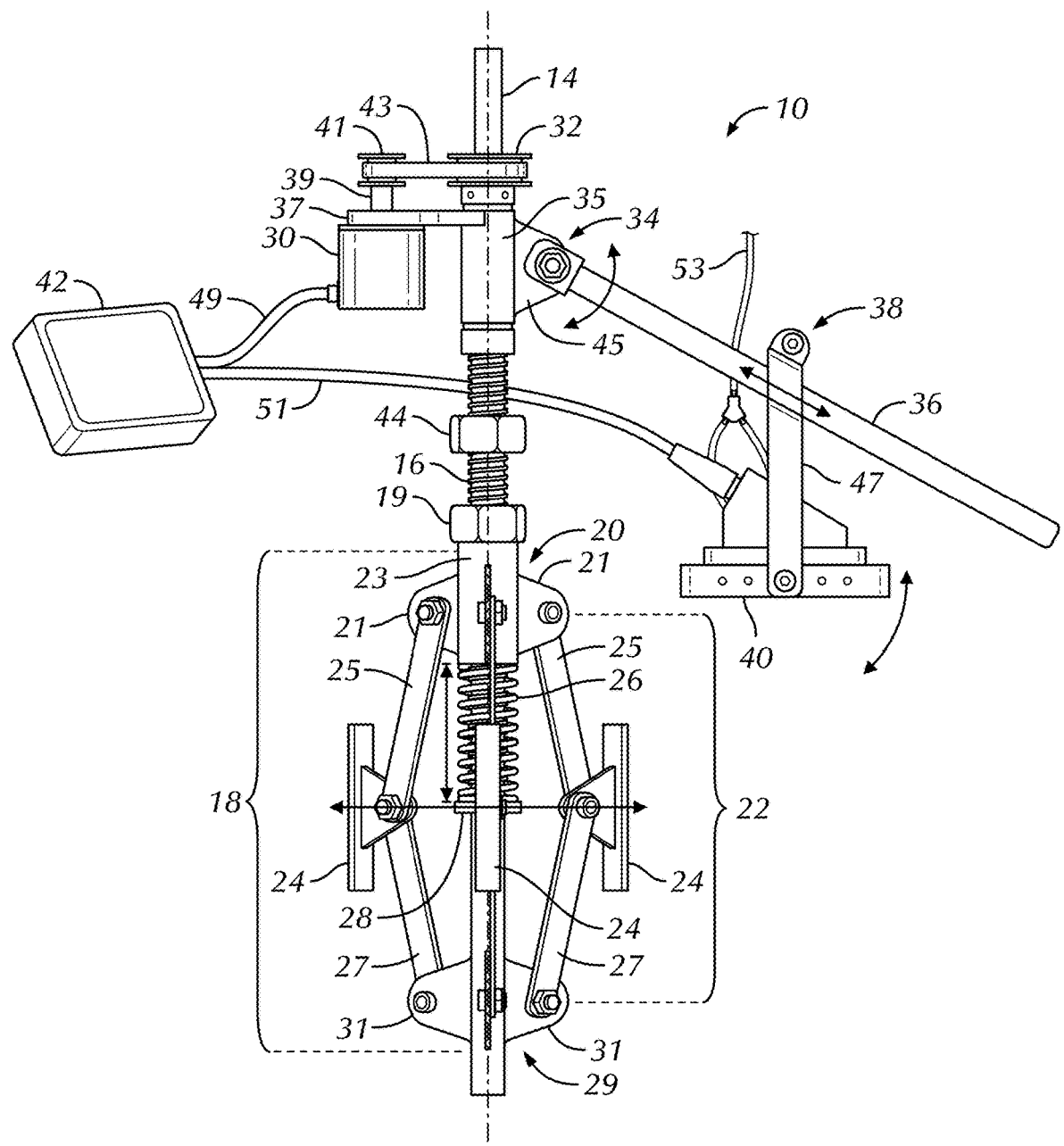
FIG. 2 is a side view of the scanner device shown in FIG. 1 showing engagement feet in a retracted position.
Figure 3:
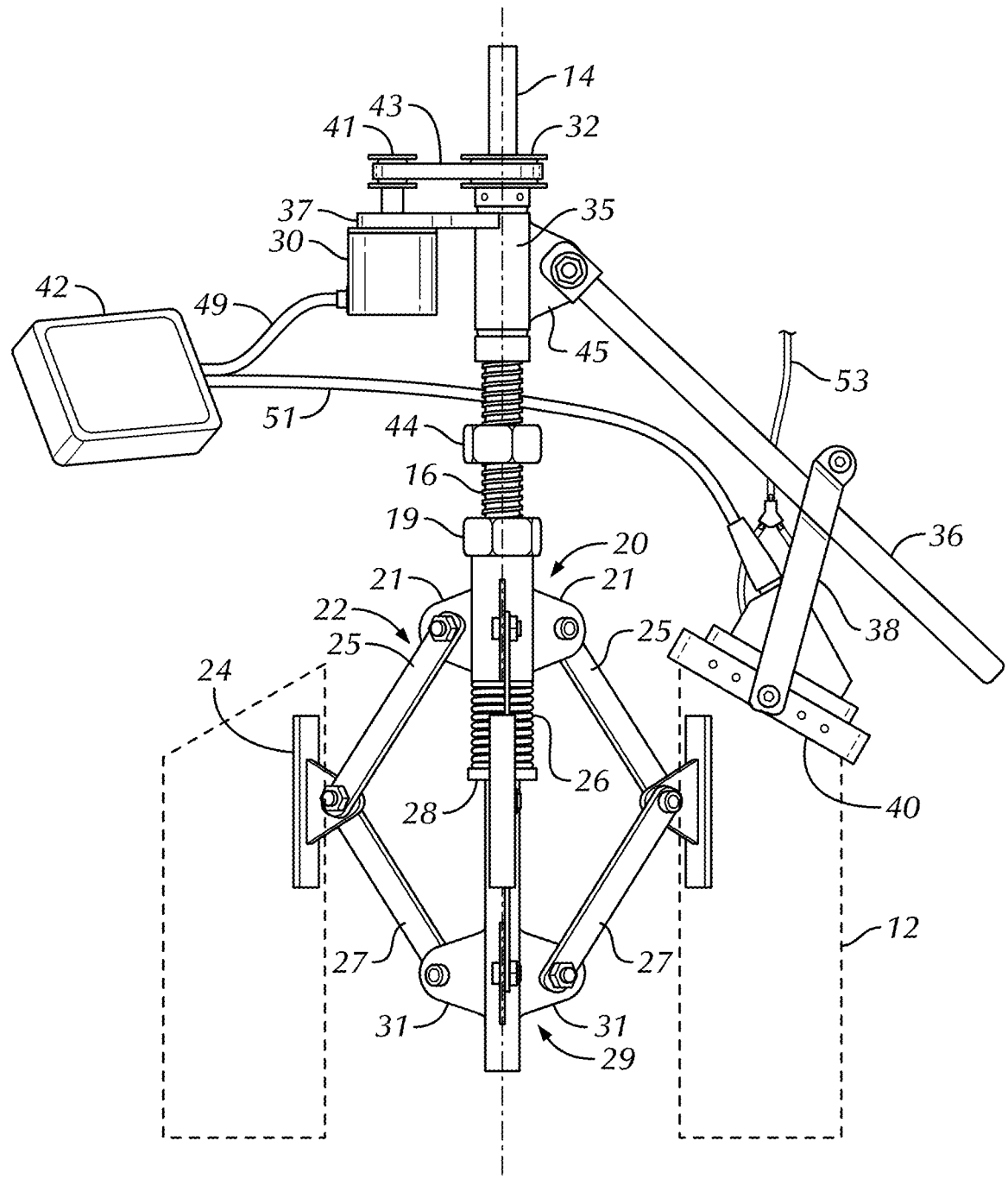
FIG. 3 is a side view of the scanned device shown in FIG. 2, but showing the engagement feet in a deployed/engaged position.
Figure 4:
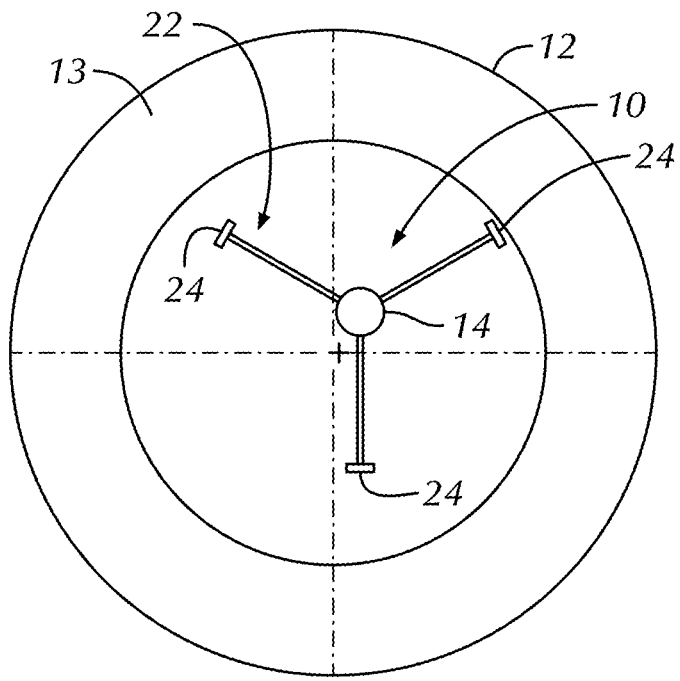
FIG. 4 is a top view showing a schematic representation of three hinged leg members attached to a vertical shaft and with engagement feet attached to each hinged leg member, with the engagement feet in a retracted position and not in contact with the part to be examined.
Figure 5:
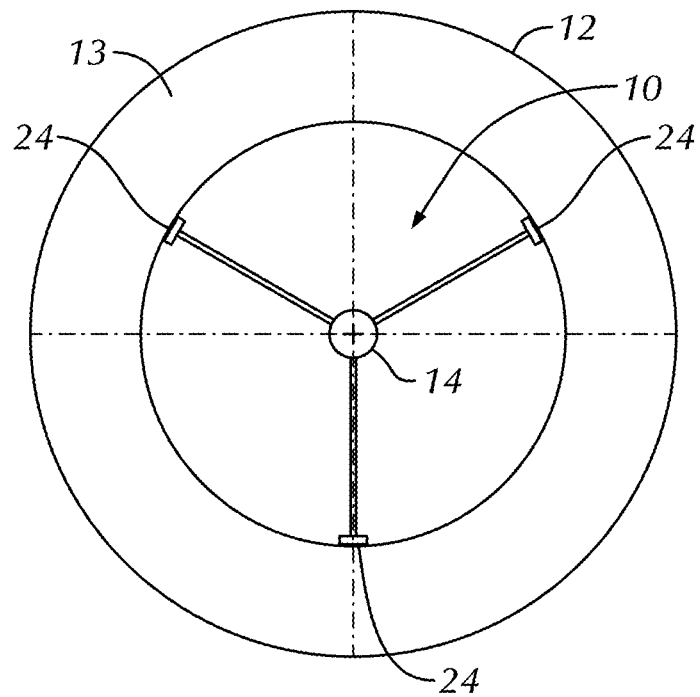
FIG. 5 is a top view similar to FIG. 4, but showing the engagement feet engaged with an inner surface of the part to be examined.

Referring to the drawings in detail, wherein like numerals denote identical elements throughout the several views, and referring initially to FIG. 1, there is shown a perspective view of a specific embodiment of a non-destructive testing (NDT) scanner device 10. FIG. 1 shows the NDT scanner device 10 mounted to a cylindrical part 12 having a beveled end 13 that is to be examined. Referring to FIGS. 2 and 3 in combination with FIG. 1, the NDT scanner device 10 includes a vertical or central shaft 14 including a lower threaded section 16. A self-centering support 18 is attached to a lower end of the central shaft 14. In a specific embodiment, the self-centering support 18 may include a slip collar 20 that is disposed around the central shaft 14, such as at a location below the lower threaded section 16 of the central shaft 14. The central shaft 14 passes or extends through an internal bore or passageway of the slip collar 20. The slip collar 20 is disposed for slidable movement relative to the central shaft 14. A threaded nut 19 is threaded onto the lower threaded section 16 of the central shaft 14 at a location above the slip collar 23. In a specific embodiment, the slip collar 20 may include a support tube 23 disposed around the central shaft 14. In a specific embodiment, the threaded nut 19 is positioned above an upper end of the support tube 23 of the slip collar 20, and with a lower surface of the threaded nut 19 in contact with the upper end of the support tube 23. A locking nut 44 is threadably attached to the lower threaded section 16 of the central shaft 14 at a location above the threaded nut 19.

In a specific embodiment, the support tube 23 of the slip collar 20 may include three support plates 21 extending radially outwardly from the support tube 23. In a specific embodiment, each support plate 21 may have a hinged leg member 22 hingedly attached thereto. Each hinged leg member 22 may include an upper arm 25, a lower arm 27, and a foot or engagement member 24. An upper end of each upper arm 25 is hingedly attached to the slip collar 20, such as to a corresponding support plate 21. A lower end of each upper arm 25 is hingedly attached to an upper end of a corresponding lower arm 27 and to a corresponding foot/engagement member 24. A lower end of each lower arm 27 is hingedly attached to a lower support 29. In a specific embodiment, the lower support 29 may be connected to a distal or lower end of the central shaft 14 or formed as part of it. In a specific embodiment, the lower support 29 may include three lower support plates 31. In a specific embodiment, the lower ends of the lower arms 27 on the hinged leg members 22 may be hingedly connected to the lower support plates 31.

A spring 26 is disposed around the central shaft 14 below the slip collar 20, and between the slip collar 20 and a shoulder 28. In a specific embodiment, the shoulder 28 may be an annular plate attached around the central shaft 14 at a location below the slip collar 20, such as toward a lower end of the central shaft 14. In a specific embodiment, the spring 26 may be positioned around the central shaft 14 and supported by the shoulder 28 at a lower end of the spring 26 and by a lower end of the support tube 23 at an upper end of the spring 26. As further discussed below, it can be seen with reference to FIGS. 2 and 3 that the threaded nut 19 can be threaded downwardly on the lower threaded section 16 of the central shaft 14, which will push the slip collar 20 downwardly, and cause the hinged leg members 22 to push the engagement feet 24 outwardly and into engagement with an inner surface of the part to be examined 12. This will "self center" the central shaft 14 within the part to be examined 12.

At the upper end of the central shaft 14, an encoder 30 is fixedly mounted to a bracket 34 that is mounted to the central shaft 14. In a specific embodiment, the upper bracket 34 and encoder 30 are positioned above the slip collar 20, the threaded nut 19, and the locking nut 44. In a specific embodiment, the bracket 34 may include a tubular member or central body member 35 disposed around the central shaft 14. In a specific embodiment, the central shaft 14 extends through an inner bore of the bracket 34, such as through an inner bore of the tubular member 35. The bracket 34 is free to rotate relative to the central shaft 14. The bracket 34 may include a generally horizontal support arm 37. The encoder 30 may be mounted to the generally horizontal support arm 37. The encoder 30 may include a drive shaft 39 that may extend upwardly in a generally vertical direction and/or that may be generally parallel to the central shaft 14. The encoder 30 may include an encoder drive pulley 41 attached to the drive shaft 39. The encoder drive pulley 41 may be connected by a belt 43 to a central pulley 32 that is fixedly mounted to the central shaft 14.

In a specific embodiment, the tubular member 25 on the bracket 34 may include a support plate 45 extending outwardly from the tubular member 25. In a specific embodiment, an elongated arm 36 is hingedly attached to the bracket 34, such as to the support plate 45, so as to allow the elongated arm 36 to be moved up and down relative to the bracket 34. A fork 38 having two legs 47 is attached to the elongated arm 36. In a specific embodiment, the fork 38 is slidably attached to the elongated arm 36 so that the fork 38 can slide up and down the elongated arm 36 in both directions to accommodate various sizes of parts to be examined 12. An ultrasonic probe 40 is attached to the fork 38 between the legs 47 of the fork 38. In a specific embodiment, the probe 40 is hingedly attached between the fork legs 47 to allow the probe to be pivoted to accommodate various angles of incline of the beveled end 13 and various configurations of parts to be examined 12, as shown for example in FIG. 1.

The encoder 30 is electrically connected to an electronic instrument 42, such as an OLYMPUS® OmniScan MX2 ultrasonic test instrument available from Olympus Corporation based in Tokyo, Japan, or a TOPAZ64 ultrasonic test instrument available from Zetec, Inc. based in Snoqualmie, Washington, for example. In a specific embodiment, the encoder is electrically connected to the electronic instrument 42 by an encoder cable 49. The ultrasonic probe 40 is also electrically connected to the electronic instrument 42. In a specific embodiment, the probe 40 is electrically connected to the electronic instrument by a probe cable 51. The cables 49 and 51 should be of sufficient length to easily allow the probe 40 and encoder 30 to rotate 360 degrees around the central shaft 14. A coupling line or tube 53 is connected to the probe 40 to supply a fluid, such as water, to the interface between the probe 40 and the surface to be inspected (e.g., beveled surface 13) to act as a medium to transmit sound from the probe 40 to the part to be inspected 12, such as the beveled surface 13.

The use and operation of the device 10 can be understood from FIG. 1-5. The self-centering support 18 is positioned inside an inner bore of the part 12 to be examined. The threaded nut 19 is threaded downwardly to push the slip collar 20 downwardly against the force of the spring 26 to push the engagement feet 24 outwardly and into contact with the inner bore of the part 12, as shown for example in FIG. 5. This centers the device 10 relative to the bore of the part to be examined 12. The locking nut 44 is threaded downwardly into contact with the top of the threaded nut 19 to lock the self-centering support 18 in place.

Next, the ultrasonic probe 40 is positioned on the beveled surface 13 of the part 12 (this is the portion of the part to be examined or tested). With the ultrasonic probe 40 held in contact with the beveled surface 13, an operator manually uses the arm 36 to move the probe 40 completely around the circumference of the beveled surface 13 of the part 12. As this is happening, the bracket 34 is being rotated relative to the central shaft 14, which causes the encoder 30 to move in an orbit around the central shaft 14, which causes the encoder shaft 39 to be rotated, which causes the encoder 30 to send a signal to the electrical instrument 42. Corresponding data from the ultrasonic probe 40 regarding the integrity of the beveled surface 13 is also being sent to the instrument 42. As such, it can be seen that the present inventions provide a way to examine or test the integrity of an end or beveled end surface (e.g., beveled surface 13) of a part to be examined (e.g., part 12) in a non-destructive manner.

It is to be understood that the inventions disclosed herein are not limited to the exact details of construction, operation, exact materials or embodiments shown and described. Although specific embodiments of the inventions have been described, various modifications, alterations, alternative constructions, and equivalents are also encompassed within the scope of the inventions. Although the present inventions may have been described using a particular series of steps, it should be apparent to those skilled in the art that the scope of the present inventions is not limited to the described series of steps. The specification and drawings are, accordingly, to be regarded in an illustrative rather than a restrictive sense. It will be evident that additions, subtractions, deletions, and other modifications and changes may be made thereunto without departing from the broader spirit and scope of the inventions as set forth in the claims set forth below. It should also be understood that various features and aspects of the various embodiments discussed above and illustrated in the Figures may be selectively incorporated with and/or removed from a specific embodiment to arrive at another specific embodiment. Accordingly, the inventions are therefore to be limited only by the scope of the appended claims. None of the claim language should be interpreted pursuant to 35 U.S.C. 112(f) unless the word "means" is recited in any of the claim language, and then only with respect to any recited "means" limitation.

The invention claimed is:

1. A scanner apparatus comprising:
a central shaft;
three engagement members supported by the central shaft, each engagement member being moveable between a first position and a second position;
an encoder supported by the central shaft and having a drive shaft coupled to the central shaft; and
an ultrasonic probe supported by and spaced apart from the central shaft, whereby movement of the ultrasonic probe around the central shaft in a first direction will cause the encoder to move around the central shaft and cause the encoder drive shaft to rotate in a second direction that is opposite to the first direction.

2. The scanner apparatus of claim 1, further including a slip collar having an internal passageway, wherein the central shaft extends through the internal passageway, the slip collar is disposed for slidable movement relative to the central shaft, and the three engagement members are supported by the slip collar.

3. The scanner apparatus of claim 2, further including three hinged leg members, each of the three hinged leg members being connected to the slip collar, each of the three engagement members being supported by one of the three hinged leg members.

4. The scanner apparatus of claim 3, wherein each of the three hinged leg members includes an upper arm and a lower arm, the upper arm having an upper end hingedly connected to the slip collar and a lower end hingedly connected to an upper end of the lower arm, the lower end of the upper arm and the upper end of the lower arm being hingedly connected to one of the three engagement members, and a lower end of the lower arm being hingedly supported the central shaft.

5. The scanner apparatus of claim 2, further including a spring disposed around the central shaft and positioned between the slip collar and a shoulder on the central shaft.

6. The scanner apparatus of claim 2, further including a threaded nut and a locking nut, the central shaft including a threaded portion, part of the threaded portion of the central shaft being positioned within the internal passageway of the slip collar, the threaded nut and the locking nut being threadably engaged with the threaded portion of the central shaft, the threaded nut being located for engagement with the slip collar, and the locking nut being located for engagement with the threaded nut.

7. The scanner apparatus of claim 1, further including a bracket having a central body member, the central body member having a longitudinal passageway therethrough, the central shaft extending through the longitudinal passageway, the bracket being rotatable relative to the central shaft, the encoder being connected to the bracket, and the ultrasonic probe being supported by the bracket.

8. The scanner apparatus of claim 7, further including an elongated arm having a first end hingedly attached to the bracket, and wherein the ultrasonic probe is connected to the elongated arm.

9. The scanner apparatus of claim 8, further including a fork having a first leg and a second leg, the ultrasonic probe being hingedly connected to the first leg and to the second leg, the fork being supported by the elongated bar and slidably moveable thereon.

10. The apparatus of claim 1, further including an electronic instrument electrically connected to the encoder and to the ultrasonic probe.

11. A scanner apparatus comprising:
a central shaft;
three engagement members supported by the central shaft, each engagement member being moveable between a first position and a second position;
a slip collar having an internal passageway, wherein the central shaft extends through the internal passageway, the slip collar is disposed for slidable movement relative to the central shaft, and the three engagement members are supported by the slip collar;
a spring disposed around the central shaft and positioned between the slip collar and a shoulder on the central shaft;
an encoder supported by the central shaft and having a drive shaft coupled to the central shaft;
an elongated arm having a first end hingedly supported by the central shaft; and
an ultrasonic probe connected to the elongated arm and spaced apart from the central shaft, whereby movement of the ultrasonic probe around the central shaft in a first direction will cause the encoder to move around the central shaft and cause the encoder drive shaft to rotate in a second direction that is opposite to the first direction.

12. The scanner apparatus of claim 11, further including three hinged leg members, each of the three hinged leg members being connected to the slip collar, each of the three engagement members being supported by one of the three hinged leg members.

13. The scanner apparatus of claim 12, wherein each of the three hinged leg members includes an upper arm and a lower arm, the upper arm having an upper end hingedly connected to the slip collar and a lower end hingedly connected to an upper end of the lower arm, the lower end of the upper arm and the upper end of the lower arm being hingedly connected to one of the three engagement members, and a lower end of the lower arm being hingedly supported the central shaft.

14. The scanner apparatus of claim 11, further including a threaded nut and a locking nut, the central shaft including a threaded portion, part of the threaded portion of the central shaft being positioned within the internal passageway of the slip collar, the threaded nut and the locking nut being threadably engaged with the threaded portion of the central shaft, the threaded nut being located for engagement with the slip collar, and the locking nut being located for engagement with the threaded nut.

15. The scanner apparatus of claim 11, further including a bracket having a central body member, the central body member having a longitudinal passageway therethrough, the central shaft extending through the longitudinal passageway, the bracket being rotatable relative to the central shaft, the encoder being connected to the bracket, and the ultrasonic probe being supported by the bracket.

16. The apparatus of claim 11, further including an electronic instrument electrically connected to the encoder and to the ultrasonic probe.

* * * * *